US010487096B2

(12) United States Patent
Gutacker et al.

(10) Patent No.: US 10,487,096 B2
(45) Date of Patent: *Nov. 26, 2019

(54) SILANES AND CURABLE COMPOSITIONS CONTAINING SAID SILANES AS CROSSLINKERS

(71) Applicant: Henkel AG & Co. KGaA, Duesseldorf (DE)

(72) Inventors: Andrea Gutacker, Langenfeld (DE); Johann Klein, Duesseldorf (DE)

(73) Assignee: Henkel AG & Co. KGaA, Duesseldorf (DE)

(*) Notice: Subject to any disclaimer, the term of this patent is extended or adjusted under 35 U.S.C. 154(b) by 116 days.

This patent is subject to a terminal disclaimer.

(21) Appl. No.: 15/702,820

(22) Filed: Sep. 13, 2017

(65) Prior Publication Data

US 2018/0002353 A1 Jan. 4, 2018

Related U.S. Application Data

(63) Continuation of application No. PCT/EP2016/055693, filed on Mar. 16, 2016.

(30) Foreign Application Priority Data

Mar. 16, 2016 (DE) .................. 10 2015 204 788

(51) Int. Cl.
| | |
|---|---|
| *C07F 7/18* | (2006.01) |
| *C08L 83/04* | (2006.01) |
| *C08G 77/388* | (2006.01) |
| *C08K 5/544* | (2006.01) |
| *C08K 5/5455* | (2006.01) |
| *C08K 5/57* | (2006.01) |
| *C07F 7/08* | (2006.01) |
| *C08G 77/16* | (2006.01) |

(52) U.S. Cl.
CPC .......... *C07F 7/1804* (2013.01); *C07F 7/1892* (2013.01); *C08G 77/388* (2013.01); *C08K 5/544* (2013.01); *C08K 5/5455* (2013.01); *C08K 5/57* (2013.01); *C08L 83/04* (2013.01); *C07F 7/0834* (2013.01); *C08G 77/16* (2013.01)

(58) Field of Classification Search
CPC ..... C07F 7/1804; C07F 7/1892; C07F 7/0834
USPC ....................................................... 556/411
See application file for complete search history.

(56) References Cited

U.S. PATENT DOCUMENTS

| | | | | |
|---|---|---|---|---|
| 4,104,296 A | * | 8/1978 | Pike .................... | C08G 77/045 |
| | | | | 556/419 |
| 4,511,728 A | | 4/1985 | Kreuzer et al. | |
| 8,569,439 B2 | | 10/2013 | Ederer et al. | |
| 9,481,817 B2 | | 11/2016 | Pichl et al. | |
| 2012/0016072 A1 | | 1/2012 | Ederer et al. | |
| 2016/0017195 A1 | * | 1/2016 | Pichl ...................... | B01J 31/04 |
| | | | | 525/477 |

FOREIGN PATENT DOCUMENTS

| | | |
|---|---|---|
| CA | 2979929 A1 | 9/2016 |
| DE | 3210337 A1 | 9/1983 |
| EP | 0564253 A1 | 10/1993 |
| EP | 1230298 B1 | 7/2003 |
| EP | 2030976 A1 | 3/2009 |
| EP | 2774672 A1 | 9/2014 |
| WO | 9933906 A1 | 7/1999 |
| WO | 2005085356 A1 | 9/2005 |
| WO | 2006099054 A2 | 9/2006 |
| WO | 2013022532 A1 | 2/2013 |
| WO | 2016146648 A1 | 9/2016 |

OTHER PUBLICATIONS

International Search Report for International PCT Patent Application No. PCT/EP2016/055693 dated Jun. 17, 2016.
M.M. Sprung in "Some α-Caraloxyalkoxy-silanes", J. Org. Chem., 1958, 23 (10), Seiten 1530-1534.
Wang et al., "B-Lactam-Forming Photochemical Reactions of . . . ", Journal of Organic Chemistry, vol. 69, 2004, pp. 1215-1220.

* cited by examiner

*Primary Examiner* — Margaret G Moore
(74) *Attorney, Agent, or Firm* — James E. Piotrowski

(57) ABSTRACT

The invention relates to a silane of the formula (1), $$Si(R^1)_m(R^2)_n(R^3)_{4-(m+n)} \quad (1)$$

as defined herein, where the silane has at least one group of the general formula (3):

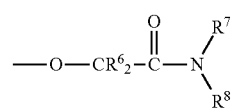

as defined herein, to a method for preparing the silane, and to curable compositions, containing the silane and at least one polyorganosiloxane.

15 Claims, No Drawings

SILANES AND CURABLE COMPOSITIONS CONTAINING SAID SILANES AS CROSSLINKERS

The invention relates to new silanes, which contain at least one special α-hydroxycarboxylic acid amide group, the preparation thereof, as well as curable compositions containing the silane and a curable polyorganosiloxane. The silane acts as a crosslinker in the curable compositions and is notable particularly for excellent stability during rather long storage as well in the mixture with other conventional components of curable compositions.

Silicone polymers (polyorganosiloxanes), particularly polydialkylsiloxanes such as polydimethylsiloxane (PDMS), have great importance in the production of adhesive, sealing, coating, and insulation materials. Among these, those that vulcanize at low temperatures and under ambient conditions constitute a not insignificant share of the market. Typical formulations contain a reactive polyorganosiloxane. As a rule, this concerns a silanol-terminated polyorganosiloxane, whereby the polyorganosiloxane has at least one, preferably two hydroxy groups bound to a silicon atom. It is used in combination with a silane-based crosslinker which has hydrolyzable groups bound to the silicon atom. The term curing agent is also used occasionally instead of crosslinker. Within the context of this application, the terms crosslinker and curing agent are synonymous. The polyorganosiloxane and crosslinker can be present as separate components. The polyorganosiloxane is often reacted selectively with the crosslinker, however, to form a modified polyorganosiloxane, and said modified polyorganosiloxane is added to the curable composition. The term endcapping (end group capping) is also used in this regard. This can be carried out optionally in the presence of a catalyst, whereby the catalyst is to mediate the endcapping selectively without simultaneously curing the polyorganosiloxane.

Numerous crosslinkers for silicone systems are known. These can be differentiated into acidic, basic, and neutral crosslinkers based on the leaving groups released during hydrolysis. Typical acidic crosslinkers contain acid groups as hydrolyzable groups and release the corresponding acids, e.g., acetic acid, during the crosslinking. Typical basic crosslinkers release amines during the crosslinking. In both cases, aggressive compounds are released during the crosslinking, which can corrode or break down, e.g., metals, stone, or mortar, and which moreover have an intense, often unpleasant odor. Neutral crosslinkers are therefore often used for modern curable silicone compositions. Typical representatives of neutral crosslinkers have hydrolyzable groups, which split off alcohol or oxime during the crosslinking. Alkoxy systems nevertheless have the disadvantage that multiple problems arise in the case of the storage stability of relevant curable compositions and the cured products exhibit only poor adhesion to some materials. Oximosilane crosslinkers, which hydrolyze with the release of an alkanone oxime, usually do not have these disadvantages and are therefore widely used. The most common representative of the oximosilane crosslinkers releases butan-2-one oxime during crosslinking. This is suspected of causing cancer, so that there is an urgent need for alternative neutral crosslinkers. Apart from that, the released oximes also have an intense, foul odor and working with curable compositions, which contain a relevant crosslinker, is perceived as disagreeable by the users.

Silane compounds that release α-hydroxycarboxylic acid esters or α-hydroxycarboxylic acid amides during crosslinking, have already been proposed therefore as alternative crosslinkers.

The preparation of suitable silane compounds has been long known and is described, for example, by M. M. Sprung in "Some α-carbalkoxyalkoxysilanes," J. Org. Chem., 1958, 23 (10), pp. 1530-1534.

DE 32 10 337 A1 as well discloses relevant silane compounds and the preparation and use thereof in curable compositions based on polydiorganosiloxanes, which have condensable end groups.

Hardeners for silicone rubber materials, which have three 2-hydroxypropionic acid alkyl ester groups, i.e., lactic acid alkyl ester groups, are known from EP 2 030 976 A1. Vinyl tris(ethyl lactato)silane is particularly preferred in this case.

EP 2 774 672 A1 describes special catalysts for the crosslinking of silicone rubber materials with a crosslinker based on a silane compound with lactate groups. Then again, the crosslinker can be the compounds known from EP 2 030 976 A1. Crosslinkers are also disclosed, however, which have only one, two, or also four 2-hydroxypropionic acid alkyl ester groups.

Although the use of a crosslinker based on a silane compound with lactate groups or similar α-carbalkoxyalkoxy groups is associated with many advantages, these crosslinkers have not yet been able to gain acceptance in practice. This is due in particular to the difficulty of formulating curable silicone-based compositions, containing these crosslinkers, such that a sufficient storage stability is achieved. The stability of the silane compound and thereby the storage stability of the curable composition deteriorate drastically specifically in the presence of other conventional and frequently indispensable components of such compositions, particularly of curing catalysts and adhesion promoters.

It is therefore an object of the present invention to provide new silane compounds that can be used as neutral crosslinkers in curable compositions based on polyorganosiloxanes, without influencing the storage stability of the curable compositions negatively.

The present invention achieves the object by providing silane compounds of the invention, which have at least one special α-hydroxycarboxylic acid amide group.

The subject matter of the invention therefore constitutes silanes of the formula (1),

$$Si(R^1)_m(R^2)_n(R^3)_{4-(m+n)} \qquad (1)$$

where
each $R^1$ independently stands for:
  a substituted or unsubstituted alkyl, alkenyl, or alkynyl group;
  a substituted or unsubstituted cycloaliphatic group or aryl group;
  a substituted or unsubstituted heteroalicyclic group or heteroaryl group;
each $R^2$ independently stands for a group of the general formula (2):

$$-O-CR^4_2-\overset{O}{\underset{\|}{C}}-O-R^5 \qquad (2)$$

where
each $R^4$ independently stands for:
  hydrogen; or
  a substituted or unsubstituted alkyl, alkenyl, or alkynyl group;
$R^5$ stands for:
  a substituted or unsubstituted alkyl, alkenyl, or alkynyl group;
for a group of the general formula (2-2):

$$-OR^{5-2} \qquad (2\text{-}2)$$

where
$R^{5-2}$ stands for:
  a substituted or unsubstituted alkyl, alkenyl, or alkynyl group;
or for a group of the general formula (2-3):

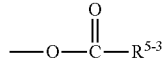
(2-3)

where
$R^{5-3}$ stands for:
  a substituted or unsubstituted alkyl, alkenyl, or alkynyl group;
each $R^3$ independently stands for a group of the general formula (3):

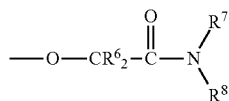
(3)

where
each $R^6$ independently stands for:
  hydrogen or
  a substituted or unsubstituted alkyl, alkenyl, or alkynyl group;
$R^7$ stands for:
  hydrogen,
  a substituted or unsubstituted alkyl, alkenyl, or alkynyl group,
  a substituted or unsubstituted cycloaliphatic group or aryl group,
  for $R^8$, or
  a group $-(CH_2)_q-COOR^9$, where p is an integer from 2 to 10, particularly 2, and $R^9$ stands for a substituted or unsubstituted alkyl, alkenyl, or alkynyl group, or a substituted or unsubstituted cycloaliphatic group or aryl group;
$R^8$ stands for a group of the general formula (4):

$$-R^{10}-SiR^{11}{}_o(OR^{12})_{3-o} \qquad (4)$$

where
$R^{10}$ stands for
  an alkylene group, optionally interrupted by a heteroatom;
each $R^{11}$ independently stands for
  a substituted or unsubstituted alkyl, alkenyl, or alkynyl group;
each $R^{12}$ independently stands for
  a substituted or unsubstituted alkyl, alkenyl, or alkynyl group,
  an acyl group; and or a group of the formula (5):

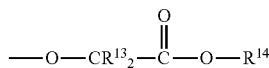
(5)

where
each $R^{13}$ independently stands for:
  hydrogen; or
  a substituted or unsubstituted alkyl, alkenyl, or alkynyl group;
$R^{14}$ stands for:
  a substituted or unsubstituted alkyl, alkenyl, or alkynyl group; and
o independently stands for 0, 1, or 2, and
m independently stands for 0 or 1 and n independently for 0, 1, 2, or 3, whereby the sum n+m is a maximum of 3.

A further subject matter of the invention is a method for preparing the silanes of the invention.

The invention relates further to curable compositions, containing at least one silane of the invention and at least one polyorganosiloxane, whereby the polyorganosiloxane has at least one hydroxy group bound to a silicon atom.

A "curable composition" is understood to be a substance or mixture of multiple substances, which is curable by physical or chemical measures. In this regard, these chemical or physical measures can be, for example, the supplying of energy in the form of heat, light, or other electromagnetic radiation, but also simply bringing into contact with atmospheric moisture, water, or a reactive component. The composition thereby changes from an original state to a state that has a higher hardness.

Provided reference is made to molecular weights of oligomers or polymers in the present application, the quantities, unless otherwise stated, refer to the weight average, i.e., the Mw value, and not to the arithmetic average. The molecular weight is determined by gel permeation chromatography (GPC) with tetrahydrofuran (THF) as the eluent according to DIN 55672-1:2007-08, preferably at 35° C. Molecular weights of monomeric compounds are calculated based on the respective molecular formula and the known molecular weights of the individual atoms.

"At least one," as used herein, refers to 1 or more, i.e., 1, 2, 3, 4, 5, 6, 7, 8, 9, or more. In regard to an ingredient, the term relates to the type of ingredient and not to the absolute number of molecules. "At least one polymer" thus means, for example, at least one type of polymer, i.e., that a type of polymer or a mixture of a number of different polymers can be used. Together with weight data, the term refers to all compounds of the given type, contained in the composition/mixture, i.e., that the composition contains no other compounds of this type beyond the given amount of the relevant compounds.

All percentage details, provided in connection with the compositions described herein, refer to % by weight, based in each case on the relevant mixture, unless explicitly indicated otherwise.

"Alkyl," as used herein, refers to a saturated aliphatic hydrocarbon including straight-chain and branched-chain groups. The alkyl group preferably has 1 to 10 carbon atoms (if a numerical range, e.g., "1-10" is given herein, this means that this group, in this case the alkyl group, can have 1 carbon atom, 2 carbon atoms, 3 carbon atoms, etc., up to and including 10 carbon atoms). In particular, the alkyl can be an intermediate alkyl, which has-5 to 6 carbon atoms, or a lower alkyl, which has 1 to 4 carbon atoms, e.g., methyl, ethyl, n-propyl, isopropyl, butyl, isobutyl, tert-butyl, etc.

The alkyl groups can be substituted or unsubstituted. "Substituted," as used in this connection, means that one or more carbon atoms and/or hydrogen atom(s) of the alkyl group are replaced by heteroatoms or functional groups. Heteroalkyl groups in which 1 or more carbon atoms are replaced by heteroatoms, particularly selected from O, S, N, and Si, are obtained by the replacement of one or more carbon atoms by heteroatoms. Examples of such heteroalkyl groups are, without limitation, methoxymethyl, ethoxyethyl, propoxypropyl, methoxyethyl, isopentoxypropyl, ethylaminoethyl, trimethoxypropylsilyl, etc. Functional groups that can replace the hydrogen atoms are selected particularly from =O, =S, —OH, —SH, —NH$_2$ —NO$_2$, —CN, —F, —Cl, —Br, —I, —OCN, —NCO, C$_{3-8}$ cycloalkyl, C$_{6-14}$ aryl, a 5-10-membered heteroaryl ring, in which 1 to 4 ring atoms independently are nitrogen, oxygen, or sulfur, and a 5-10-membered heteroalicyclic ring, in which 1 to 3 ring atoms are independently nitrogen, oxygen, or sulfur.

"Alkenyl," as used herein, refers to an alkyl group, as defined herein, which consists of at least two carbon atoms and at least one carbon-carbon double bond, e.g., ethenyl, propenyl, butenyl, or pentenyl and structural isomers thereof such as 1- or 2-propenyl, 1-, 2-, or 3-butenyl, etc. Alkenyl groups can be substituted or unsubstituted. If they are substituted, the substituents are as defined above for alkyl.

"Alkynyl," as used herein, refers to an alkyl group, as defined herein, which consists of at least two carbon atoms and at least one carbon-carbon triple bond, e.g., ethynyl (acetylene), propynyl, butynyl, or petynyl and structural isomers thereof as described above. Alkynyl groups can be substituted or unsubstituted. If they are substituted, the substituents are as defined above for alkyl.

A "cycloaliphatic group" or "cycloalkyl group," as used herein, refers to monocyclic or polycyclic groups (a number of rings with carbon atoms in common), particularly of 3-8 carbon atoms, in which the ring does not have a completely conjugated pi-electron system, e.g., cyclopropyl, cyclobutyl, cyclopentyl, cyclohexyl, cyclobutenyl, cyclopentenyl, cyclohexenyl, etc. Cycloalkyl groups can be substituted or unsubstituted. "Substituted," as used in this regard, means that one or more hydrogen atoms of the cycloalkyl group are replaced by functional groups. Functional groups that can replace the hydrogen atoms are selected particularly from =O, =S, —OH, —SH, —NH$_2$ —NO$_2$, —CN, —F, —Cl, —Br, —I, —OCN, —NCO, C$_{1-10}$ alkyl, C$_{2-10}$ alkenyl, C$_{2-10}$ alkynyl, C$_{3-8}$ cycloalkyl, C$_{6-14}$ aryl, a 5-10-membered heteroaryl ring, in which 1 to 4 ring atoms independently are nitrogen, oxygen, or sulfur, and a 5-10-membered heteroalicyclic ring, in which 1 to 3 ring atoms independently are nitrogen, oxygen, or sulfur.

"Aryl," as used herein, refers to monocyclic or polycyclic groups (i.e., rings that have neighboring carbon atoms in common), particularly of 6 to 14 carbon ring atoms which have a completely conjugated pi-electron system. Examples of aryl groups are phenyl, naphthalenyl, and anthracenyl. Aryl groups can be substituted or unsubstituted. If they are substituted, the substituents are as defined above for cycloalkyl.

A "heteroaryl" group, as used herein, refers to a monocyclic or polycyclic (i.e., rings that share an adjacent ring atom pair) aromatic ring, having particularly 5 to 10 ring atoms, where one, two, three, or four ring atoms are nitrogen, oxygen, or sulfur and the rest is carbon. Examples of heteroaryl groups are pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, isobenzofuryl, benzothienyl, benzotriazolyl, isobenzothienyl, indolyl, isoindolyl, 3H-indolyl, benzimidazolyl, benzothiazolyl, benzoxazolyl, quinolizinyl, quinazolinyl, phthalazinyl, quinoxalinyl, cinnolinyl, naphthyridinyl, quinolyl, isoquinolyl, tetrazolyl, 5,6,7,8-tetrahydroquinolyl, 5,6,7,8-tetrahydroisoquinolyl, purinyl, pteridinyl, pyridinyl, pyrimidinyl, carbazolyl, xanthenyl, or benzoquinolyl. Heteroaryl groups can be substituted or unsubstituted. If they are substituted, the substituents are as defined above for cycloalkyl.

A "heteroalicyclic group" or a "heterocycloalkyl group," as used herein, refers to a monocyclic or fused ring having 5 to 10 ring atoms, which contains one, two, or three heteroatoms, selected from N, O, and S, whereby the rest of the ring atoms are carbon. A "heterocycloalkenyl" group contains in addition one or more double bonds. The ring however has no completely conjugated pi-electron system. Examples of heteroalicyclic groups are pyrrolidinone, piperidine, piperazine, morpholine, imidazolidine, tetrahydropyridazine, tetrahydrofuran, thiomorpholine, tetrahydropyridine, and the like. Heterocycloalkyl groups can be substituted or unsubstituted. If they are substituted, the substituents are as defined above for cycloalkyl.

The silanes of the invention are silanes of the formula (1):

$$Si(R^1)_m(R^2)_n(R^3)_{4-(m+n)} \quad (1).$$

In this case, each $R^1$ independently stands for a substituted or unsubstituted alkyl, alkenyl, or alkynyl group; a substituted or unsubstituted cycloaliphatic group or aryl group; or a substituted or unsubstituted heteroalicyclic group or heteroaryl group.

Preferably, each $R^1$ independently of one another stands for an alkyl group having 1 to 10 carbon atoms, preferably having 1 to 4 carbon atoms, particularly methyl, ethyl, propyl, or isopropyl, for an alkenyl group having 2 to 10 carbon atoms, preferably 2 to 4 carbon atoms, particularly vinyl or allyl, or an aryl group having 6 to 10 carbon atoms, particularly phenyl.

Particularly preferably, $R^1$ independently of one another stands for methyl, vinyl, or phenyl, very particularly preferably for methyl or vinyl.

In formula (1), each $R^2$ independently of one another stands for a group of the general formula (2):

$$—OCR^4{}_2COOR^5 \quad (2),$$

where
each $R^4$ independently stands for:
hydrogen; or
a substituted or unsubstituted alkyl, alkenyl, or alkynyl group; and
$R^5$ stands for:
a substituted or unsubstituted alkyl, alkenyl, or alkynyl group,
for a group of the general formula (2-2):

$$—OR^{5-2} \quad (2-2)$$

where
$R^{5-2}$ stands for:
a substituted or unsubstituted alkyl, alkenyl, or alkynyl group;
or for a group of the general formula (2-3):

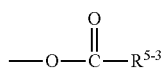

(2-3)

where
R⁵⁻³ stands for:
a substituted or unsubstituted alkyl, alkenyl, or alkynyl group.

In other words, $R^2$ is an α-hydroxycarboxylic acid ester group, an alkoxy group, or an acyloxy group.

Preferably each $R^2$ independently of one another stands for a group of the formula (2), whereby one of the $R^4$ groups stands for hydrogen and the second $R^4$ group for hydrogen or a substituted or unsubstituted alkyl group having 1 to 10 carbon atoms, preferably an unsubstituted alkyl group having 1 to 10 carbon atoms, preferably having 1 to 4 carbon atoms, particularly methyl, and/or, preferably and, $R^5$ stands for a substituted or unsubstituted alkyl group having 1 to 10 carbon atoms, preferably an unsubstituted alkyl group having 1 to 10 carbon atoms, particularly having 1 to 4 carbon atoms, particularly preferably methyl or ethyl.

Particularly preferably, each $R^2$ independently of one another stands for a group of the formula (2), where one $R^4$ group stands for hydrogen and the second $R^4$ group for methyl, and $R^5$ for ethyl.

Alternatively, at least one $R^2$ stands for a group of the formula (2-2) or a group of the formula (2-3), preferably for a group of the formula (2-2). In this case, $R^{5-2}$ and $R^{5-3}$ each preferably stand for a substituted or unsubstituted alkyl group having 1 to 10 carbon atoms, particularly having 1 to 4 carbon atoms, particularly preferably methyl or ethyl.

In a particular embodiment of the invention, each $R^2$ independently of one another stands for a group of the formula (2-2), where $R^{5-2}$ stands for a substituted or unsubstituted alkyl group having 1 to 10 carbon atoms, particularly having 1 to 4 carbon atoms, particularly preferably methyl or ethyl.

In formula (1), each $R^3$ independently of one another stands for a group of the general formula (3):

$$—OCR^6{}_2CONR^7R^8 \quad (3).$$

In other words, $R^3$ is an α-hydroxycarboxylic acid amide group.

In this case, each $R^6$ independently stands for
hydrogen or
a substituted or unsubstituted alkyl, alkenyl, or alkynyl group;
$R^7$ stands for:
hydrogen,
a substituted or unsubstituted alkyl, alkenyl, or alkynyl group, a substituted or unsubstituted cycloaliphatic group or aryl group, for $R^8$, or
a group —$(CH_2)_q$—$COOR^9$, where p is an integer from 2 to 10, particularly 2, and $R^9$ stands for a substituted or unsubstituted alkyl, alkenyl, or alkynyl group, or a substituted or unsubstituted cycloaliphatic group or aryl group;
$R^8$ stands for a group of the general formula (4):

$$—R^{10}—SiR^{10}{}_o(OR^{12})_{3-o} \quad (4)$$

where
$R^{10}$ stands for:
an alkylene group, optionally interrupted by a heteroatom;
each $R^{11}$ independently stands for:
a substituted or unsubstituted alkyl, alkenyl, or alkynyl group;
each $R^{12}$ independently stands for:
a substituted or unsubstituted alkyl, alkenyl, or alkynyl group,
an acyl group, or a group of the formula (5):

$$—CR^{13}{}_2COOR^{14} \quad (5)$$

where
each $R^{13}$ independently stands for:
hydrogen; or
a substituted or unsubstituted alkyl, alkenyl, or alkynyl group;
$R^{14}$ stands for:
a substituted or unsubstituted alkyl, alkenyl, or alkynyl group; and
o independently stands for 0, 1, or 2, and
m independently stands for 0 or 1 and n independently for 0, 1, 2, or 3, whereby the sum n+m is a maximum of 3.

Preferably, one of the $R^6$ groups stands for hydrogen and the second $R^6$ group for hydrogen or a substituted or unsubstituted alkyl group having 1 to 10 carbon atoms, preferably an unsubstituted alkyl group having 1 to 10 carbon atoms, preferably having 1 to 4 carbon atoms, particularly methyl.

$R^7$ preferably stands for hydrogen, a substituted or unsubstituted alkyl group having 1 to 10 carbon atoms, preferably an unsubstituted alkyl group having 1 to 10 carbon atoms, particularly having 1 to 4 carbon atoms, particularly methyl, or for $R^8$.

$R^{10}$ preferably is an alkylene group of the formula —$(CH_2)_p$—, where p is an integer from 1 to 6, particularly 3.

Each $R^{11}$ preferably independently of one another stands for a substituted or unsubstituted alkyl group having 1 to 10 carbon atoms, preferably an unsubstituted alkyl group having 1 to 10 carbon atoms, particularly having 1 to 4 carbon atoms, particularly preferably methyl or ethyl.

Each $R^{12}$ independently of one another preferably stands for a substituted or unsubstituted alkyl group having 1 to 10 carbon atoms, preferably an unsubstituted alkyl group having 1 to 10 carbon atoms, particularly having 1 to 4 carbon atoms, particularly preferably methyl or ethyl.

Each $R^{13}$ preferably stands for hydrogen or a substituted or unsubstituted alkyl group having 1 to 10 carbon atoms, preferably an unsubstituted alkyl group having 1 to 10 carbon atoms, preferably having 1 to 4 carbon atoms, particularly methyl. Particularly preferably, one $R^{13}$ group stands for hydrogen and the second $R^{13}$ group for hydrogen or a substituted or unsubstituted alkyl group having 1 to 10 carbon atoms, preferably an unsubstituted alkyl group having 1 to 10 carbon atoms, preferably having 1 to 4 carbon atoms, particularly methyl.

$R^{14}$ preferably stands for a substituted or unsubstituted alkyl group having 1 to 10 carbon atoms, preferably an unsubstituted alkyl group having 1 to 10 carbon atoms, preferably having 1 to 4 carbon atoms, particularly preferably methyl or ethyl.

o stands for 0, 1 or 2, preferably for 0 or 1, particularly preferably for 0.

Preferably each $R^3$ independently of one another stands for a group of the formula (3), whereby one of the $R^6$ groups stands for hydrogen and the second $R^e$ group for hydrogen or a substituted or unsubstituted alkyl group having 1 to 10 carbon atoms, preferably an unsubstituted alkyl group having 1 to 10 carbon atoms, preferably having 1 to 4 carbon atoms, particularly methyl, $R^7$ for hydrogen, a substituted or unsubstituted alkyl group having 1 to 10 carbon atoms, preferably an unsubstituted alkyl group having 1 to 10 carbon atoms, particularly having 1 to 4 carbon atoms, particularly methyl, and $R^8$ for a group of the formula (4), whereby $R^{10}$ is an alkylene group of the formula —$(CH_2)_p$—, where p is an integer from 1 to 6, particularly 3, each $R^{11}$ independently of one another for a substituted or unsubstituted alkyl group having 1 to 10 carbon atoms, preferably an unsubstituted alkyl group having 1 to 10 carbon atoms, particularly having 1 to 4 carbon atoms, particularly preferably methyl or ethyl, and each $R^{12}$ independently of one another for a substituted or unsubstituted alkyl group having 1 to 10 carbon atoms, preferably an unsubstituted alkyl group having 1 to 10 carbon atoms, particularly having 1 to 4 carbon atoms, particularly preferably methyl or ethyl, and o for 0, 1, or 2, preferably 0 or 1.

Particularly preferably each $R^3$ independently of one another stands for a group of the formula (3), where one of the $R^6$ groups stands for hydrogen and the second $R^6$ group for methyl, $R^7$ for hydrogen or methyl, and $R^8$ for a group of the formula (4), where $R^{10}$ is an alkylene group of the formula —$(CH_2)_p$—, where p stands for 3, each $R^{11}$ independently of one another stands for methyl or ethyl, and each $R^{12}$ independently of one another for methyl or ethyl, and o for 0, 1, or 2, preferably 0 or 1, particularly preferably 0.

In formula (1), n and m are selected so that the sum n+m is a maximum of 3; i.e., the silane of the formula (1) contains at least one $R^3$ group, i.e., at least one α-hydroxycarboxylic acid amide group. n in this case stands for 0 or 1, preferably for 1. m stands for 0, 1, 2, or 3, preferably for 0, 1, or 2, particularly preferably for 2.

Very particularly preferred silanes of the formula (1) are selected from compounds, obtained by selective amidation of methyl tris(ethyl lactato)silane, ethyl tris(ethyl lactato) silane, phenyl tris(ethyl lactato)silane, vinyl tris(ethyl lactato)silane, tetra(ethyl lactato)silane, or mixtures thereof with an amine of the formula (6):

(HR$^7$N)—R$^{10}$—SiR$^{11}_o$(OR$^{12}$)$_{3-o}$     (6)

where
o, $R^7$, $R^{10}$, and each $R^{11}$ and each $R^{12}$, in each case independently of one another, have the aforesaid general, preferred, and particularly preferred meanings. Particularly preferably, this concerns an amidation product of methyl tris(ethyl lactato)silane, ethyl tris(ethyl lactato)silane, phenyl tris(ethyl lactato)silane, vinyl tris(ethyl lactato)silane, tetra(ethyl lactato)silane, or mixtures thereof with 3-aminopropyltrimethoxysilane and/or 3-aminopropyltriethoxysilane.

The subject matter of the invention, furthermore, is a method for preparing the silanes of the invention, whereby a silane of the formula (5),

Si(R$^1$)$_m$(R$^2$)$_{4-m}$     (5)

where
m, as well as each $R^1$ and each $R^2$ in each case independently of one another, have the aforesaid general, preferred, and particularly preferred meanings,
and at least one aminosilane compound of the general formula (6):

(HR$^7$N)—R$^{10}$—SiR$^{11}_o$(OR$^{12}$)$_{3-o}$     (6)

where
o, $R^7$, $R^{10}$, and each $R^{11}$ and each $R^{12}$, in each case independently of one another, have the aforesaid general, preferred, and particularly preferred meanings,
are reacted with one another.

Preferably, in this case, the molar ratio of the silane of the formula (5) to the aminosilane compound of the general formula (6) is 2:1 to 30:1, particularly preferably 4:1 to 15:1.

Preferably, the silane of the formula (5) and the aminosilane compound of the general formula (6) are reacted at normal pressure (1 bar) and a temperature of 40 to 80° C., preferably 50 to 80° C., particularly preferably 60 to 80° C. For this purpose, the aforesaid educts are stirred together, preferably for at least 10 minutes, preferably for at least 30 minutes, particularly preferably for at least 60 minutes.

A further subject matter of the invention is curable compositions, containing at least one silane of the formula (1) and at least one polyorganosiloxane, whereby the polyorganosiloxane has at least one hydroxy group bound to a silicon atom.

The curable compositions contain the silane of the formula (1) preferably in an amount of 2 to 7% by weight, particularly preferably in an amount of 4 to 6% by weight, based in each case on the total weight of the composition. If a mixture of a number of silanes of the formula (1) is used, the quantitative data naturally refer to the total amount of silanes of the formula (1) in the composition.

The curable compositions, moreover, contain at least one polyorganosiloxane, which has at least one hydroxy group bound to a silicon atom. Preferably, the polyorganosiloxane has at least two hydroxy groups bound to a silicon atom. It is preferred, in addition, that the hydroxy group or hydroxy groups are bound to terminal silicon atoms. If the polyorganosiloxane is branched, it preferably has a hydroxy group at each end.

The polyorganosiloxane, which has at least one hydroxy group bound to a silicon atom, is preferably a polydiorganosiloxane, preferably a polydimethylsiloxane.

Preferably, therefore, an α,ω-dihydroxy-terminated polydiorganosiloxane, particularly an α,ω-dihydroxy-terminated polydimethylsiloxane is used as the polyorganosiloxane, which has at least one hydroxy group bound to a silicon atom. Particularly preferred are α,ω-dihydroxy-terminated polydimethylsiloxanes, which have a kinematic viscosity at 25° C. of 5000 to 120,000 cSt, particularly 10,000 to 100,000 cSt, and particularly preferably 50,000 to 90,000 cSt.

The curable compositions contain the at least one polyorganosiloxane, which has at least one hydroxy group bound to a silicon atom, preferably in an amount of 30 to 90% by weight, particularly preferably in an amount of 40 to 60% by weight, based in each case on the total weight of the composition. If a mixture of a number of polyorganosiloxanes is used, the quantitative data naturally relate to the total amount of the polyorganosiloxanes, which have at least one hydroxy group bound to a silicon atom, in the composition.

The curable compositions can contain the polyorganosiloxane, which has at least one hydroxy group bound to a silicon atom, and the silane of the formula (1) as separate components. It is likewise possible, however, that these components are present in the form of a prepolymer. The prepolymer is a reaction product of the two components. Suitable reactions are known and are also called endcapping. This can be carried out optionally in the presence of a catalyst, whereby the catalyst is to mediate the endcapping selectively without simultaneously curing the polyorganosiloxane. Suitable catalysts are, for example, acids, organic lithium compounds, as they are described, for example, in EP 0 564 253 A1, amines, inorganic oxides, potassium acetate, organotitanium derivatives, titanium/amine combinations, and carboxylic acid/amine combinations.

If the polyorganosiloxane, which has at least one hydroxy group bound to a silicon atom, and the silane of the formula (1) are present as a prepolymer, thus the aforesaid quantitative data for polyorganosiloxane, on the one hand, and the silane, on the other, for the prepolymer are to be applied additively. The curable compositions, therefore, contain the prepolymer preferably in an amount of 32 to 97% by weight, particularly preferably in an amount of 44 to 66% by weight, based in each case on the total weight of the composition. If a mixture of a number of prepolymers is used, the quantitative data naturally refer to the total amount of prepolymers in the composition.

The compositions of the invention crosslink in the presence of moisture and in so doing cure with the formation of Si—O—Si bonds. Said curing can be accelerated by the addition of a suitable curing catalyst.

Preferably, the curable composition therefore contains further at least one curing catalyst, particularly a tin compound.

Preferably, this is an organotin compound or an inorganic tin salt. Tin in these tin compounds is preferably bivalent or tetravalent. Suitable inorganic tin salts are, for example, tin(II) chloride and tin(IV) chloride. Organotin compounds (tin organyles) are used preferably as tin compounds, however. Suitable organotin compounds are, for example, the 1,3-dicarbonyl compounds of bivalent or tetravalent tin, for example, the acetylacetonates such as di(n-butyl)tin(IV) di(acetylacetonate), di(n-octyl)tin(IV) di(acetylacetonate), (n-octyl)(n-butyl)tin(IV) di(acetylacetonate); the dialkyl tin (IV) dicarboxylates, for example, di-n-butyltin dilaurate, di-n-butyltin maleate, di-n-butyltin diacetate, di-n-octyltin dilaurate, di-n-octyltin diacetate, or the corresponding dialkoxylates, for example, di-n-butyltin dimethoxide; oxides of tetravalent tin, for example, dialkyltin oxides, such as, for example, di-n-butyltin oxide and Di-n-octyltin oxide; and the tin(II) carboxylates such as tin(II) octoate or tin(II) phenolate.

Suitable furthermore are tin compounds of ethyl silicate, dimethyl maleate, diethyl maleate, dioctyl maleate, dimethyl phthalate, diethyl phthalate, dioctyl phthalate, such as, for example, di(n-butyl)tin(IV) di(methyl maleate), di(n-butyl) tin(IV) di(butyl maleate), di(n-octyl)tin(IV) di(methyl maleate), di(n-octyl)tin(IV) di(butyl maleate), di(n-octyl)tin (IV) di(isooctyl maleate); and di(n-butyl)tin(IV) sulfide, (n-butyl)$_2$Sn(SCH$_2$COO), (n-octyl)$_2$Sn(SCH$_2$COO), (n-octyl)$_2$Sn(SCH$_2$CH$_2$COO), (n-octyl)$_2$Sn (SCH$_2$CH$_2$COOCH$_2$CH$_2$OCOCH$_2$S), (n-butyl)$_2$-Sn (SCH$_2$COO-i-C$_8$H$_{17}$)$_2$, (n-octyl)$_2$Sn(SCH$_2$COO-i-C$_8$H$_{17}$)$_2$, and (n-octyl)$_2$Sn(SCH$_2$COO-n-C$_8$H$_{17}$)$_2$.

Preferably, the tin compound is selected from 1,3-dicarbonyl compounds of bivalent or tetravalent tin, the dialkyltin (IV) dicarboxylates, the dialkyltin(IV) dialkoxylates, the dialkyltin(IV) oxides, the tin(II) carboxylates, and mixtures thereof.

Particularly preferably, the tin compound is a dialkyltin (IV) dicarboxylate, particularly di-n-butyltin dilaurate or di-n-octyltin dilaurate.

Tin-free curing catalysts can be used in addition to or instead of the aforesaid tin compounds. The tin compounds in fact exhibit very high catalytic activity, but are suspected in part of being hazardous to health. In a particular embodiment, the compositions therefore contain exclusively tin-free curing catalysts; i.e., they are free of tin.

Suitable tin-free curing catalysts are, for example, organometallic compounds of iron, particularly the 1,3-dicarbonyl compounds of iron such as, e.g., iron(III) acetylacetonate.

Boron halides such as boron trifluoride, boron trichloride, boron tribromide, boron triiodide, or mixtures of boron halides can also be used as curing catalysts. Particularly preferred are boron trifluoride complexes such as, e.g., boron trifluoride diethyl etherate, which as liquids are easier to handle than gaseous boron halides.

Further, amines, nitrogen heterocycles, and guanidine derivatives are suitable in general for catalysis. An especially suitable catalyst from this group is 1,8-diazabicyclo [5.4.0]undec-7-ene (DBU).

In addition, preferably titanium, aluminum, and zirconium compounds, or mixtures of one or more catalysts from one or more of the just mentioned groups are used as catalysts. On the one hand, the use of tin compounds can be avoided in this way as well, and, on the other, a better adhesion to normally poorly adherent organic surfaces such as, e.g., acrylates can be achieved. Of the titanium, aluminum, and zirconium catalysts, the titanium catalysts are used with preference, because the best curing results are achieved with them.

Suitable as titanium catalysts are compounds that have hydroxy groups and/or substituted or unsubstituted alkoxy groups, therefore titanium alkoxides of the general formula

Ti(OR$^z$)$_4$, where R$^z$ is an organic group, preferably a substituted or unsubstituted hydrocarbon group having 1 to 20 C atoms, and the 4 alkoxy groups —OR$^z$ are identical or different. Further, one or more of the —OR$^z$ groups can be replaced by acyloxy groups —OCOR$^z$.

Likewise suitable as titanium catalysts are titanium alkoxides in which one or more alkoxy groups are replaced by a hydroxy group or halogen atoms.

Further, titanium chelate complexes can be used.

Aluminum catalysts can also be used as curing catalysts, e.g., aluminum alkoxides

Al(OR$^z$)$^3$, where R$^z$ has the above meaning; i.e., it is an organic group, preferably a substituted or unsubstituted hydrocarbon group having 1 to 20 C atoms and the three R$^z$ groups are identical or different. In the case of aluminum alkoxides as well, one or more of the alkoxy groups can be replaced by acyloxy groups —OC(O)R$^z$.

Further, aluminum alkoxides can be used in which one or more alkoxy groups are replaced by a hydroxy group or halogen atoms.

Of the described aluminum catalysts, the pure aluminum alcoholates are preferred in regard to their stability to moisture and the curability of the mixtures to which they are added. In addition, aluminum chelate complexes are preferred.

Suitable as zirconium catalysts are, e.g.: tetramethoxyzirconium or tetraethoxyzirconium.

Diisopropoxyzirconium bis(ethyl acetoacetate), triisopropoxyzirconium (ethyl acetoacetate), and isopropoxyzirconium tris(ethyl acetoacetate) are used with very particular preference.

Further, zirconium acylates can be used, for example.

Halogenated zirconium catalysts can also be used.

Further, zirconium chelate complexes can also be used.

In addition, carboxylic acid salts of metals or also a mixture of a number of such salts can be employed as curing catalysts, whereby these are selected from the carboxylates of the following metals: calcium, vanadium, iron, zinc, titanium, potassium, barium, manganese, nickel, cobalt, and/or zirconium.

Of the carboxylates, the calcium, vanadium, iron, zinc, titanium, potassium, barium, manganese, and zirconium carboxylates are preferred, because they exhibit a high activity. Calcium, vanadium, iron, zinc, titanium, and zirconium carboxylates are particularly preferred. Iron and titanium carboxylates are very particularly preferred.

The curable compositions contain the curing catalyst preferably in an amount of 0.01 to 2% by weight, preferably in an amount of 0.05 to 2% by weight, particularly preferably in an amount of 0.1 to 0.5% by weight, based in each case on the total weight of the composition. If a mixture of a number of curing catalysts is used, the quantitative data naturally refer to the total amount of curing catalyst in the composition.

The curable compositions can contain, apart from the aforesaid components, one or more components that can be used to influence specific properties of the curable composition and/or the cured product selectively.

These other components can be selected, for example, from the group comprising plasticizers, stabilizers, antioxidants, fillers, reactive diluents, drying agents, adhesion promoters, UV stabilizers, rheological aids, and/or solvents. In this case, particular importance is attached to adhesion promoters, plasticizers, fillers, and stabilizers, comprising antioxidants and UV stabilizers.

Preferably the curable compositions therefore contain at least one further component.

The curable composition of the invention can therefore contain in addition one or more adhesion promoters. An adhesion promoter is understood to be a substance that improves the adhesion properties of adhesive layers on surfaces.

Conventional adhesion promoters (tackifiers), known to the skilled artisan can be used alone or as a combination of a number of compounds. Suitable are, for example, resins, terpene oligomers, coumarone/indene resins, aliphatic petrochemical resins and modified phenol resins. Suitable within the context of the present invention are, for example, hydrocarbon resins, as can be obtained by polymerization of terpenes, primarily α- or β-pinene, dipentene, or limonene. These monomers are generally polymerized cationically with initiation using Friedel-Crafts catalysts. The terpene resins also include copolymers of terpenes and other monomers, for example, styrene, α-methylstyrene, isoprene, and the like. The aforesaid resins are used, for example, as adhesion promoters for contact adhesives and coating materials. Likewise suitable are terpene-phenol resins, which are prepared by the acid-catalyzed addition of phenols to terpenes or rosin. Terpene-phenol resins are soluble in most organic solvents and oils and miscible with other resins, waxes, and caoutchouc. Likewise suitable as an adhesion promoter in the aforesaid sense within the context of the present invention are the rosin resins and derivatives thereof, for example, the esters or alcohols thereof.

Especially highly suitable are silane adhesion promoters, particularly alkoxysilanes, with a (further) functional group such as, e.g., an amino group, a mercapto group, an epoxy group, a carboxyl group, a vinyl group, an isocyanate group, an isocyanurate group, or a halogen. Examples are γ-mercaptopropyltrimethoxysilane, γ-mercaptopropyltriethoxysilane, γ-mercaptopropylmethyldimethoxysilane, γ-glycidoxypropyltrimethoxysilane, γ-glycidoxypropyltriethoxysilane, γ-glycidoxypropylmethyldimethoxysilane, β-carboxyethyltriethoxysilane, β-carboxyethylphenylbis(2-methoxyethoxy)silane, N-β-(carboxymethyl)aminoethyl-γ-aminopropyltrimethoxysilane, vinyltrimethoxysilane, vinyltriethoxysilane, γ-acroyloxypropylmethytriethoxysilane, γ-isocyanato-propyltrimethoxysilane, γ-isocyanatopropyltriethoxysilane, γ-isocyanatopropylmethyldiethoxysilane, γ-isocyanatopropylmethyldimethoxysilane, tris(trimethoxysilyl)isocyanurate, and γ-chloropropyltrimethoxysilane.

Especially preferred as adhesion promoters are in particular aminosilanes (aminofunctional alkoxysilanes or aminoalkylalkoxysilanes), such as, e.g., γ-aminopropyltrimethoxysilane, γ-aminopropyltriethoxysilane, γ-aminopropyltriisopropoxysilane, γ-aminopropylmethyldimethoxysilane, γ-aminopropylmethyldiethoxysilane, γ-(2-aminoethyl)-3-aminopropyltrimethoxysilane, γ-(2-aminoethyl)aminopropylmethyldimethoxysilane, γ-(2-aminoethyl)aminopropyltriethoxysilane, γ-(2-aminoethyl)aminopropylmethyldiethoxysilane, γ-(2-aminoethyl)aminopropyltriisopropoxysilane, N-phenyl-γ-aminopropyltrimethoxysilane, N-benzene-γ-aminopropyltrimethoxysilane, and N-vinylbenzyl-γ-aminopropyltriethoxysilane, or oligomeric aminosilanes, such as, e.g., aminoalkyl group-modified alkylpolysiloxane (Dynasylan 1146).

Preferred, furthermore, as an adhesion promoter is a silane of the general formula (7)

where

R$^{13}$ and R$^{14}$ independently of one another are hydrogen or C$_1$-C$_8$ alkyl groups, R' is a divalent hydrocarbon group, optionally containing a heteroatom and having 1-12 C atoms, and X', Y', Z' independently of one another are C$_1$-C$_8$ alkyl, C$_1$-C$_8$ alkoxy, or C$_1$-C$_8$ acyloxy groups, at least one of the groups being a C$_1$-C$_8$ alkoxy or C$_1$-C$_8$ acyloxy moiety or group.

Such compounds naturally have a high affinity for the binding polymer components of the curable composition of the invention, but also for a large range of polar and nonpolar surfaces and for this reason contribute to the formation of an especially stable adhesion between the adhesive or sealant composition and the substrates to be glued or sealed in each case.

The linking group R' can be, for example, a straight-chain or branched or cyclic, substituted or unsubstituted alkylene group. The hydrocarbon group can be saturated or unsaturated. Optionally, nitrogen (N) or oxygen (O) is present therein as a heteroatom. Preferably, R' is a hydrocarbon group having 1 to 6 C atoms, particularly having 1 to 3 C atoms, for example, methylene or n-propylene.

X', Y', and Z' preferably are each, independently of one another, a methyl, an ethyl, a methoxy, or an ethoxy group. Particularly preferably, X', Y', and Z' are alkoxy groups, particularly methoxy groups. Very particularly preferably, the group —SiX'Y'Z' is a trimethoxy or dimethoxymethylsilyl group. If X', Y', and/or Z' are an acyloxy group, it can be, e.g., the acetoxy group —OCO—CH$_3$.

An aminosilane compound of the general formula (6), as described above, is used particularly preferably as an adhesion promoter. It can be used therefore for preparing the silane of the formula (1), and can also assume the function of an adhesion promoter in the curable composition.

The curable compositions contain the adhesion promoter preferably in an amount of up to 20% by weight, primarily in an amount of 0.05 to 4% by weight, preferably in an amount of 0.1 to 2% by weight, particularly preferably in an amount of 0.2 to 2% by weight, based in each case on the total weight of the composition. If a mixture of a number of adhesion promoters is used, the quantitative data naturally refer to the total amount of adhesion promoters in the composition.

It is conceivable that the viscosity of the curable composition is too high for certain applications. It can then be reduced in a simple and expedient way usually by using a reactive diluent, without any signs of demixing (e.g., plasticizer migration) occurring in the cured mass.

Preferably, the reactive diluent has at least one functional group which after application reacts, e.g., with moisture or atmospheric oxygen. Examples of groups of this type are silyl groups, isocyanate groups, vinylically unsaturated groups, and polyunsaturated systems.

All compounds that can be mixed with the other components with a reduction in viscosity and have at least one group reactive with the polymer can be used as reactive diluents.

The viscosity of the reactive diluent is preferably less than 20,000 mPas, particularly preferably about 0.1 to 6000 mPas, very particularly preferably 1 to 1000 mPas (Brookfield RVT, 23° C., spindle 7, 10 rpm).

The following substances, for example, can be used as reactive diluents: polyalkylene glycols reacted with isocyanatosilanes (e.g., Synalox 100-50B, DOW), carbamatopropyltrimethoxysilane, alkyltrimethoxysilane, alkyltriethoxysilane, such as methyltnrimethoxysilane, methyltriethoxysilane, and vinyltrimethoxysilane (XL 10, Wacker), vinyltriethoxysilane, phenyltrimethoxysilane, phenyltriethoxysilane, octyltrimethoxysilane, tetraethoxysilane, vinyldimethoxymethylsilane (XL12, Wacker), vinyltriethoxysilane (GF56, Wacker), vinyltriacetoxysilane (GF62, Wacker), isooctyltrimethoxysilane (10 Trimethoxy), isooctyltriethoxysilane (10 Triethoxy, Wacker), N-trimethoxysilylmethyl-O-methyl carbamate (XL63, Wacker), N-dimethoxy(methyl)silylmethyl-O-methyl carbamate (XL65, Wacker), hexadecyltrimethoxysilane, 3-octanoylthio-1-propyltriethoxysilane, and partial hydrolysates of said compounds.

Further, the following polymers from Kaneka Corp. can also be used as reactive diluents: MS S203H, MS S303H, MS SAT 010, and MS SAX 350.

Silane-modified polyethers which derive, e.g., from the reaction of isocyanatosilane with Synalox types can likewise be used.

Polymers that can be prepared from an organic framework by grafting with a vinylsilane or by reacting polyol, polyisocyanate, and alkoxysilane can be used, furthermore, as reactive diluents.

A polyol is understood to be a compound that may contain one or more OH groups in the molecule. The OH groups can be both primary and secondary.

Suitable aliphatic alcohols include, for example, ethylene glycol, propylene glycol, and higher glycols, as well as other polyfunctional alcohols. The polyols can contain in addition other functional groups such as. e.g., esters, carbonates, or amides.

To prepare the preferred reactive diluents, the corresponding polyol component is reacted in each case with an at least difunctional isocyanate. Any isocyanate having at least two isocyanate groups may basically be used as the at least difunctional isocyanate, but within the scope of the present invention, compounds with two to four isocyanate groups, particularly with two isocyanate groups, are generally preferred.

Preferably, the compound present as the reactive diluent has at least one alkoxysilyl group, whereby of the alkoxysilyl groups, the di- and trialkoxysilyl groups are preferred.

Suitable as polyisocyanates for the preparation of a reactive diluent are, for example, ethylene diisocyanate, 1,4-tetramethylene diisocyanate, 1,4-tetramethoxybutane diisocyanate, 1,6-hexamethylene diisocyanate (HDI), cyclobutane-1,3-diisocyanate, cyclohexane-1,3 and -1,4 diisocyanate, bis(2-isocyanatoethyl) fumarate, as well as mixtures of two or more thereof, 1-isocyanato-3,3,5-trimethyl-5-isocyanatomethyl cyclohexane (isophorone diisocyanate, IPDI), 2,4- and 2,6-hexahydrotoluylene diisocyanate, hexahydro-1,3- or -1,4-phenylene diisocyanate, benzidine diisocyanate, naphthalene-1,5-diisocyanate, 1,6-diisocyanato-2,2,4-trimethylhexane, 1,6-diisocyanato-2,4,4-trimethylhexane, xylylene diisocyanate (XDI), tetramethylxylylene diisocyanate (TMXDI), 1,3- and 1,4-phenylene diisocyanate, 2,4- or 2,6-toluylene diisocyanate (TDI), 2,4'-diphenylmethane diisocyanate, 2,2'-diphenylmethane diisocyanate, or 4,4'-diphenylmethane diisocyanate (MDI), or the partially or completely hydrogenated cycloalkyl derivatives thereof, for example, completely hydrogenated MDI (H12-MDI), alkyl-substituted diphenylmethane diisocyanates, for example, mono-, di-, tri-, or tetraalkyl diphenylmethane diisocyanate and the partially or completely hydrogenated cycloalkyl derivatives thereof, 4,4'-diisocyanatophenyl perfluoroethane, phthalic acid bis-isocyanatoethyl ester, 1-chloromethylphenyl-2,4- or -2,6-diisocyanate, 1-bromomethylphenyl-2,4- or -2,6-diisocyanate, 3,3-bis-chloromethyl ether-4,4'-diphenyl diisocyanate, sulfur-containing diisocyanates, as can be obtained by reacting 2 mol of diisocyanate with 1 mol of thiodiglycol or dihydroxydihexyl sulfide, the di- and triisocyanates of dimer and trimer fatty acids, or mixtures of two or more of the aforesaid diisocyanates.

Trivalent or higher-valent isocyanates, as can be obtained, for example, by oligomerization of diisocyanates, particularly by oligomerization of the aforesaid isocyanates, can also be used as polyisocyanates. Examples of such trivalent and higher-valent polyisocyanates are the triisocyanurates of HDI or IPDI or mixtures thereof or mixed triisocyanurates thereof, as well as polyphenylmethylene polyisocyanate, as can be obtained by phosgenation of aniline-formaldehyde condensation products.

Solvents and/or plasticizers can be used, in addition to or instead of a reactive diluent, for reducing the viscosity of the curable composition.

Suitable as solvents are aliphatic or aromatic hydrocarbons, halogenated hydrocarbons, ketones, ethers, esters, ester alcohols, keto alcohols, keto ethers, keto esters, and ether esters.

The composition described herein furthermore can contain hydrophilic plasticizers. These are used to improve the moisture absorption and thereby to improve the reactivity at low temperatures. Suitable as plasticizers are, for example, esters of abietic acid, adipic acid esters, azelaic acid esters, benzoic acid esters, butyric acid esters, acetic acid esters, esters of higher fatty acids having approximately 8 to approximately 44 carbon atoms, epoxidized fatty acids, fatty acid esters and fats, glycolic acid esters, phosphoric acid esters, phthalic acid esters, linear or branched alcohols containing 1 to 12 carbon atoms, propionic acid esters, sebacic acid esters, sulfonic acid esters, thiobutyric acid esters, trimellitic acid esters, citric acid esters, and esters based on nitrocellulose and polyvinyl acetate, as well as mixtures of two or more thereof.

For example, of the phthalic acid esters, dioctyl phthalate, dibutyl phthalate, diisoundecyl phthalate, or butylbenzyl phthalate is suitable, and of the adipates, dioctyl adipate, diisodecyl adipate, diisodecyl succinate, dibutyl sebacate, or butyl oleate.

Likewise suitable as plasticizers are the pure or mixed ethers of monofunctional, linear or branched $C_{4-16}$ alcohols or mixtures of two or more different ethers of such alcohols, for example, dioctyl ether (obtainable as Cetiol OE, Cognis Deutschland GmbH, Düsseldorf).

Endcapped polyethylene glycols are suitable further as plasticizers, for example, polyethylene or polypropylene glycol di-$C_{1-4}$-alkyl ethers, particularly the dimethyl or diethyl ethers of diethylene glycol or dipropylene glycol, and mixtures of two or more thereof.

Particularly preferred as plasticizers, however, are endcapped polyethylene glycols, such as polyethylene or polypropylene glycol dialkyl ethers, where the alkyl group has up to four C atoms, and particularly the dimethyl and diethyl ethers of diethylene glycol and dipropylene glycol. An acceptable curing is achieved in particular with dimethyldiethylene glycol also under less favorable application conditions (low humidity, low temperature). Reference is made to the relevant technical chemistry literature for further details on plasticizers.

Likewise suitable as plasticizers within the scope of the present invention are diurethanes, which can be prepared, for example, by reacting diols, having OH end groups, with monofunctional isocyanates, by selecting the stoichiometry such that substantially all free OH groups react. Optionally excess isocyanate can then be removed from the reaction mixture, for example, by distillation. A further method for preparing diurethanes consists of reacting monofunctional alcohols with diisocyanates, whereby all NCO groups are reacted if possible.

Preferably, the curable composition has at least one plasticizer, particularly a polydimethylsiloxane.

The curable compositions contain the reactive diluents, the solvent and/or the plasticizer preferably in an amount of 1 to 50% by weight, preferably in an amount of 10 to 40% by weight, particularly preferably in an amount of 20 to 30% by weight, based in each case on the total weight of the composition. If a mixture of a number of reactive diluents, solvents, and/or plasticizers is used, the quantitative data naturally refer to the total amount of reactive diluents, solvents, and/or plasticizers in the composition.

Preferably, the curable composition contains at least one stabilizer, selected from antioxidants, UV stabilizers, and drying agents.

All conventional antioxidants may be used as antioxidants. They are preferably present up to about 7% by weight, particularly up to about 5% by weight.

The composition herein can contain UV stabilizers, which are preferably used up to about 2% by weight, preferably about 1% by weight. The so-called hindered amine light stabilizers (HALS) are particularly suitable as UV stabilizers. It is preferred within the context of the present invention if a UV stabilizer is employed, which carries a silyl group and is incorporated into the end product during crosslinking or curing. The products Lowilite 75 and Lowilite 77 (Great Lakes, USA) are particularly suitable for this purpose. Further, benzotriazoles, benzophenones, benzoates, cyanoacrylates, acrylates, sterically hindered phenols, phosphorus, and/or sulfur can also be added.

It is often useful to stabilize the compositions in regard to penetrating moisture by means of drying agents in order to increase the storability (shelf life) still further.

Such an improvement in storability can be achieved, for example, by using drying agents. All compounds that react with water with the formation of a group inert to the reactive groups present in the preparation are suitable as drying agents and thereby undergo the smallest possible changes in their molecular weight. Furthermore, the reactivity of the drying agents to moisture penetrating into the preparation must be higher than the reactivity of the groups of the silyl group-bearing polymer of the invention present in the preparation Isocyanates, for example, are suitable as drying agents.

Advantageously, however, silanes are used as drying agents. For example, vinylsilanes such as 3-vinylpropyltriethoxysilane, oxime silanes such as methyl-O,O',O''-butan-2-one-trioximosilane or O,O',O'',O'''-butan-2-one-tetraoximosilane (CAS Nos. 022984-54-9 and 034206-40-1) or benzamidosilanes such as bis(N-methylbenzamido)methylethoxysilane (CAS No. 16230-35-6) or carbamatosilanes such as carbamatomethyltrimethoxysilane. The use of methyl-, ethyl-, or vinyltrimethoxysilane, tetramethyl- or tetraethylethoxysilane is also possible, however. Vinyltrimethoxysilane and tetraethoxysilane are particularly preferred in terms of cost and efficiency.

Likewise suitable as drying agents are the aforesaid reactive diluents, provided they have a molecular weight ($M_n$) of less than about 5000 g/mol and have end groups whose reactivity to penetrated moisture is at least as high as, preferably higher than, the reactivity of the reactive groups of the polymer used according to the invention.

Lastly, alkyl orthoformates or alkyl orthoacetates can also be used as drying agents, for example, methyl or ethyl orthoformate or methyl or ethyl orthoacetate, The compositions generally contain about 0 to about 6% by weight of drying agent.

The composition described herein can contain fillers in addition. Suitable here are, for example, chalk, lime powder, precipitated and/or pyrogenic silicic acid, zeolites, bentonites, magnesium carbonate, kieselguhr, alumina, clay, talc, titanium oxide, iron oxide, zinc oxide, sand, quartz, flint, mica, glass powder, and other ground mineral substances. Organic fillers can also be used, furthermore, particularly carbon black, graphite, wood fibers, wood flour, sawdust, cellulose, cotton, pulp, cotton, wood chips, chopped straw, and chaff. Further, short fibers such as glass fibers, glass filament, polyacrylonitrile, carbon fibers, Kevlar fibers, or polyethylene fibers as well can also be added. Aluminum powder is likewise suitable as a filler.

The pyrogenic and/or precipitated silicic acids advantageously have a BET surface area of 10 to 90 $m^2/g$. When they are used, they do not cause any additional increase in the viscosity of the composition of the invention, but contribute to strengthening the cured composition.

It is likewise conceivable to use pyrogenic and/or precipitated silicic acids with a higher BET surface area, advantageously with 100 to 250 $m^2/g$, particularly 110 to 170 $m^2/g$, as a filler. Because of the higher BET surface area, the same effect, e.g., strengthening of the cured preparation, can be achieved at a smaller weight proportion of silicic acid. Further substances can thus be used to improve the composition described herein in terms of other requirements.

Suitable further as fillers are hollow spheres having a mineral shell or a plastic shell. These can be, for example, hollow glass spheres which are obtainable commercially under the trade names Glass Bubbles®. Plastic-based hollow spheres, e.g., Expancel® or Dualite®, are described, for example, in EP 0 520 426 B1. They are made up of inorganic or organic substances and each have a diameter of 1 mm or less, preferably 500 µm or less.

Fillers that impart thixotropy to the preparations are preferred for many applications. Such fillers are also described as rheological adjuvants, e.g., hydrogenated castor oil, fatty acid amides, or swellable plastics such as PVC. In order to be readily squeezable out of a suitable dispensing device (e.g., a tube), such preparations possess a viscosity from 3000 to 15,000, preferably 40,000 to 80,000 mPas, or even 50,000 to 60,000 mPas.

The fillers are preferably used in an amount of 1 to 80% by weight, particularly preferably 2 to 20% by weight, and very particularly preferably 5 to 10% by weight, based in each case on the total weight of the composition. Of course, mixtures of a number of fillers can also be used. In this case, the quantitative data naturally refer to the total amount of filler in the composition.

The preparation of the curable composition can take place by simple mixing of the polyorganosiloxane, which has at least one hydroxy group bound to a silicon atom, of the silane of the formula (1), and optionally the other ingredients. This can take place in suitable dispersing units, e.g., a high-speed mixer. In this case, preferably, care is taken that the mixture does not come into contact with moisture as far as possible, which could lead to an undesirable premature curing. Suitable measures are sufficiently known and comprise, for example, working in an inert atmosphere, possibly under a protective gas, and drying/heating of individual components before they are added.

A preferred production method comprises mixing the polyorganosiloxane, which has at least one hydroxy group bound to a silicon atom, and the silane of the formula (1) in a first step, whereby this can take place in the presence of at least one aminosilane and at least one plasticizer, in a second step optionally adding other ingredients with the exception of the curing catalyst and mixing all ingredients, and in a third step lastly adding a curing catalyst and mixing it with the other components.

The subject matter of the invention, moreover, is the use of the compositions of the invention as an adhesive or sealing or coating material.

The composition or preparation can be used as an adhesive, sealant, surfacer, and for the production of molded parts. A further field of application for the compositions is the use as a plugging compound, hole filler, or crack filler.

The compositions and preparations are therefore suitable for bonding plastics, metals, glass, ceramic, wood, wood-based materials, paper, paper-based materials, rubber, and textiles, for gluing floors, and for sealing building elements, windows, wall and floor coverings, and joints in general. In this case, the materials can be bonded to themselves or as desired to one another.

The following examples serve to explain the invention, but the invention is not limited thereto.

EXAMPLES

Example 1: Preparation of a Silane of the Formula (1)

5.5 g of vinyl tris(ethyl lactato)silane was mixed with 0.4 g of 3-aminopropyltriethoxysilane and heated to 70° C. The reaction mixture was stirred for an hour at 70° C. The NMR spectroscopy analysis of the reaction product showed that cleavage of ethanol and amidation of ethyl lactate groups have occurred. A silane of the formula (1) results.

Comparative Example 1 (VB1)

The comparison composition VB1 was prepared from the raw materials listed in Table 1. For this purpose, the polymer (α,ω-dihydroxy-terminated polydimethylsiloxane) and plasticizer were charged with the curing agent vinyl tris(ethyl lactato)silane and 3-aminopropyltriethoxysilane and stirred for 5 minutes and then vacuum is applied for 5 minutes. Next, the highly dispersed silicic acid was added with stirring and the mixture was evacuated. Lastly, the remaining aminosilanes and the catalyst were added and incorporated for 10 minutes under vacuum.

Example 2 (B2)

The composition of the invention B2 was prepared from the raw materials listed in Table 1. For this purpose, first a silane of the formula (1) was prepared according to Example 1 from vinyl tris(ethyl lactato)silane and 3-aminopropyltriethoxysilane and without an intermediate purification, it was combined with the polymer (α,ω-dihydroxy-terminated polydimethylsiloxane) and plasticizer and the mixture was stirred for 5 minutes and then vacuum was applied for 5 minutes. Next, the highly dispersed silicic acid was added with stirring and the mixture was evacuated. Lastly, the remaining aminosilanes and the catalyst were added and incorporated for 10 minutes under vacuum.

The prepared formulations VB1 and B2 were analyzed with respect to skin-over time, hardness, extensibility, and elongation and with respect to adhesion properties on different substrates. All tests were carried out with the freshly formulated composition and after 4 and 12 weeks of aging at 40° C./80% relative humidity. The results for the comparison formulation VB1 are presented in Table 2, and the results for the formulation of the invention B2 in Table 3.

A comparison of the results for the comparison formulation VB1 and formulation of the invention B2 shows that when the silane of the invention was used an improved curing behavior (shorter skin-over times with comparable to slightly improved curing depths) can be achieved, and the mechanical properties of the cured products are comparable. In addition, when the silane of the invention was used, an excellent adhesion (Cf1) was consistently achieved in all tested substrates, whereas the comparison formulations exhibited weaknesses during bonding of aluminum and wood.

TABLE 1

| Raw materials | VB1 % by weight | B2 % by weight |
|---|---|---|
| α,ω-Dihydroxy-terminated polydimethylsiloxane with a viscosity of 80,000 cST | 49.2 | 49.2 |
| Polydimethylsiloxane with a viscosity of 1000 cST (plasticizer) | 36.4 | 36.4 |
| Vinyl tris(ethyl lactato)silane | 5.5 | |
| 3-Aminopropyltriethoxysilane | 0.4 | |
| Silane of the formula (1) (vinyl tris(ethyl lactato)silane and 3-aminopropyltriethoxysilane were mixed in a weight ratio of 55:4 and reacted for 1 hour at 70° C.) | | 5.9 |
| Highly dispersed silicic acid | 7.4 | 7.4 |
| Aminosilane (mixture of I) bis[3-(trimethoxysilyl)propyl]amine and II) reaction product of 3-(N,N-dimethylamino)propyltrimethoxysilane and OH-terminated polydimethylsiloxane, whereby I) and II) are present in a weight ratio of 15:7) | 0.85 | 0.85 |
| Curing catalyst (di-n-butyltin dilaurate (DBTL)) | 0.25 | 0.25 |

TABLE 2

Properties of the comparison formulation VB1

| Formulation VB1 | fresh | 4 weeks of storage at 40% relative humidity and 80° C. | 12 weeks of storage at 40% relative humidity and 80° C. |
| --- | --- | --- | --- |
| Skin-over time (min) | 7 | 20 | 30 |
| Shore A 1d | 15 | 13 | 8 |
| Shore A 7d | 25 | 22 | 22 |
| Curing depth (mm/24 h) | 4.1 | 4.2 | 4.2 |
| E modulus at 100% (N/mm$^2$) | 0.31 | n.d. | 0.24 |
| Breaking force (N/mm$^2$) | 1.2 | n.d. | 1.2 |
| Elongation at break (%) | 548 | n.d. | 574 |
| Adhesion | | | |
| PVC | Cf1 | Cf1 | Cf1 |
| Brass | Cf1 | Cf1 | Cf1 |
| Glass | Cf1 | Cf1 | Cf1 |
| Aluminum (E6EV1) | Af1 | Af2 | Af2 |
| Tiles | Cf1 | Cf1 | Cf1 |
| GRP | Cf1 | Cf1 | Cf1 |
| Wood | Cf1 | Af1 | Af2 | n.d.: not determined
GRP: glass fiber-reinforced plastic

TABLE 3

Properties of the formulation of the invention B2

| Formulation B2 | Fresh | 4 weeks of storage at 40% relative humidity and 80° C. | 12 weeks of storage at 40% relative humidity and 80° C. |
| --- | --- | --- | --- |
| Skin-over time (min) | 6 | 8 | 18 |
| Shore A 1d | 14 | 13 | 7 |
| Shore A 7d | 25 | 22 | 20 |
| Curing depth (mm/24 h) | 4.0 | 4.5 | 4.3 |
| E modulus at 100% (N/mm$^2$) | 0.29 | n.d. | 0.24 |
| Breaking force (N/mm$^2$) | 1.1 | n.d. | 0.9 |
| Elongation at break (%) | 523 | n.d. | 443 |
| Adhesion | | | |
| PVC | Cf1 | Cf1 | Cf1 |
| Brass | Cf1 | Cf1 | Cf1 |
| Glass | Cf1 | Cf1 | Cf1 |
| Aluminum (E6EV1) | Cf1 | Cf1 | Cf1 |
| Tiles | Cf1 | Cf1 | Cf1 |
| GRP | Cf1 | Cf1 | Cf1 |
| Wood | Cf1 | Cf1 | Cf1 | n.d.: not determined
GRP: glass fiber-reinforced plastic

Measuring the Skin-Over Time:

The skin-over time is determined under standard climatic conditions (23+/−2° C., relative humidity 50+/−5%). The temperature of the sealant must be 23+/−2° C.; the sealant is to be stored beforehand for at least 24 hours in the laboratory. The sealant is applied to a sheet of paper and drawn out to a skin with a putty knife (thickness of about 2 mm, width of about 7 cm). A stopwatch is started immediately. The surface is touched lightly with the fingertip and the finger is removed again; the surface is pressed so greatly that an impression remains on the surface until the skin-over time is reached. The skin-over time is reached when sealant no longer adheres to the fingertip. The skin-over time is given in minutes.

Measuring the Shore a Hardness:
The procedure follows ISO 868.
Measuring Curing Depth:

A sealant strand with a height of 10 mm (+/−1 mm) and a width of 20 mm (+/−2 mm) is applied with an appropriate spatula to a plastic card. After storage for 24 hours under standard climatic conditions (23+/−2° C., relative humidity 50+/−5%), a piece is cut out of the strand and the thickness of the cured layer is measured using a vernier caliper. The curing depth is given in [mm/24 h].

Measuring the Mechanical Properties (Tensile Test):

The breaking force, elongation at break, and tensile stress values (E modulus) are determined in accordance with DIN 53504 using the tensile test.

Deviation from the Norm:

Dumbbell specimens with the following dimensions are used as the test pieces: thickness: 2+/−0.2 mm; gauge width: 10+/−0.5 mm; gauge length: about. 45 mm; total length: 9 cm. The test is carried out under standard climatic conditions (23+/−2° C., 50+/−5% rel. humidity). The test takes place after 7 days of curing.

Procedure:

A 2 mm-thick film is drawn out of the material. The film is stored for 7 days under standard climatic conditions and the dumbbells are then punched out. Three dumbbells are to be made for each test. The test is to be carried out under standard climatic conditions. The specimens must be acclimatized to the test temperature (i.e., stored) for at least 20 minutes before the measurement. Before the measurement, the thickness of the test specimens is to be measured at least 3 places at room temperature using a vernier caliper; i.e., in the case of the dumbbells, preferably the ends and the middle within the initial gauge length are to be measured. In the case of elastic materials, it is advisable in addition to measure the transverse gauge. The average value is to be entered in the measuring program. The test specimens are to be clamped in the tensile testing machine so that the longitudinal axis coincides with the mechanical axis of the tensile testing machine and the largest possible surface of the grips is grasped, without the narrow section being clamped. At a test speed of 50 mm/min, the dumbbell is tensioned to a preload of <0.1 MPa. The force-elongation curve is then recorded at a test speed of 50 mm/min.

Assessment: The following values are to be obtained from the measurement: breaking force in [N/mm$^2$], elongation at break in [%], and E modulus at 100% elongation in [N/mm]

Measurement of Adhesion Properties:

The procedure was as follows for evaluating the adhesion properties of the compositions to a substrate:

Before the composition is applied, nonabsorbent substrates are cleaned with a solvent mixture consisting of acetone and isopropanol (mixing ratio of 1:3). Next, 3 beads each (about 1.5 cm wide and about 3 mm thick) of the material to be analyzed are applied to the substrate to be tested. The adhesion of the material is evaluated in each case after 2 weeks of prestorage under standard climatic conditions (23±2° C.) and (50±5% rel. humidity). For this purpose, one bead each is loosened about 1 cm from the substrate using a knife. The attempt is made to completely remove the bead by pulling on this piece at an angle of about 90°. The fracture between sealant and substrate is evaluated. The following are differentiated:

Af=adhesive failure
Cf=cohesive failure

Additional differentiation by scores of 1 to 3: 1="considerable adhesion" to 3="no adhesion"

The invention claimed is:

1. A silane of the formula (1), $$Si(R^1)_m(R^2)_n(R^3)_{4-(m+n)} \quad (1)$$

where
each m is independently 0 or 1, each n is independently 0, 1, 2, or 3, and the sum n+m is a maximum of 3;
each $R^1$ independently stands for:
   a substituted or unsubstituted alkyl, alkenyl or alkynyl group,
   a substituted or unsubstituted cycloaliphatic group or aryl group, or
   a substituted or unsubstituted heteroalicyclic group or heteroaryl group;
each $R^2$ independently stands for a group of the general formula (2):

$$-O-CR^4_2-\overset{O}{\overset{\|}{C}}-O-R^5 \quad (2)$$

where
each $R^4$ independently stands for:
   hydrogen, or
   a substituted or unsubstituted alkyl, alkenyl, or alkynyl group;
$R^5$ stands for:
   a substituted or unsubstituted alkyl, alkenyl, or alkynyl group, or
   a group of the general formula (2-2):

$$-OR^{5-2} \quad (2-2)$$

where
$R^{5-2}$ stands for:
   a substituted or unsubstituted alkyl, alkenyl, or alkynyl group; or
   a group of the general formula (2-3):

$$-O-\overset{O}{\overset{\|}{C}}-R^{5-3} \quad (2-3)$$

where
$R^{5-3}$ stands for:
   a substituted or unsubstituted alkyl, alkenyl, or alkynyl group;
each $R^3$ independently stands for a group of the general formula (3):

$$-O-CR^6_2-\overset{O}{\overset{\|}{C}}-N\overset{R^7}{\underset{R^8}{}} \quad (3)$$

where
each $R^6$ independently stands for:
   hydrogen or a substituted or unsubstituted alkyl, alkenyl, or alkynyl group;
$R^7$ stands for:
   hydrogen,
   a substituted or unsubstituted alkyl, alkenyl, or alkynyl group,
   a substituted or unsubstituted cycloaliphatic group or aryl group,
   $R^8$, or
   a group $-(CH_2)_q-COOR^9$, where p is an integer from 2 to 10, and $R^9$ stands for a substituted or unsubstituted alkyl, alkenyl, or alkynyl group, or a substituted or unsubstituted cycloaliphatic group or aryl group;
$R^8$ stands for a group of the general formula (4):

$$-R^{10}-SiR^{11}_o(OR^{12})_{3-o} \quad (4)$$

where
o independently stands for 0, 1, or 2,
$R^{10}$ stands for an alkylene group, optionally interrupted by a heteroatom,
each $R^{11}$ independently stands for a substituted or unsubstituted alkyl, alkenyl, or alkynyl group,
each $R^{12}$ independently stands for:
   a substituted or unsubstituted alkyl, alkenyl, or alkynyl group,
   an acyl group;
   or a group of the formula (5):

$$-O-CR^{13}_2-\overset{O}{\overset{\|}{C}}-O-R^{14} \quad (5)$$

where
each $R^{13}$ independently stands for:
   hydrogen; or
   a substituted or unsubstituted alkyl, alkenyl, or alkynyl group;
$R^{14}$ stands for:
   a substituted or unsubstituted alkyl, alkenyl, or alkynyl group.

2. The silane according to claim 1, wherein each $R^1$ independently of one another stands for an alkyl group having 1 to 10 carbon atoms, or for an alkenyl group having 2 to 10 carbon atoms.

3. The silane according to claim 1, wherein each $R^2$ independently of one another stands for a group of the formula (2), one of the $R^4$ groups stands for hydrogen and the second $R^4$ group stands for hydrogen or a substituted or unsubstituted alkyl group having 1 to 10 carbon atoms, and/or $R^5$ stands for a substituted or unsubstituted alkyl group having 1 to 10 carbon atoms.

4. The silane according to claim 1, wherein each $R^2$ independently of one another stands for a group of the formula (2-2), where $R^{5-2}$ stands for a substituted or unsubstituted alkyl group having 1 to 10 carbon atoms.

5. The silane according to claim 1, wherein each $R^3$ independently of one another stands for a group of the formula (3), one of the $R^6$ groups stands for hydrogen and the second $R^6$ group stands for hydrogen or a substituted or unsubstituted alkyl group having 1 to 10 carbon atoms.

6. The silane according to claim 1, wherein each $R^3$ independently of one another stands for a group of the formula (3), and $R^7$ stands for hydrogen, a substituted or unsubstituted alkyl group having 1 to 10 carbon atoms or $R^8$.

7. The silane according to claim 1, wherein each $R^3$ independently of one another stands for a group of the formula (3), $R^8$ stands for a group of the formula (4), $R^{10}$ stands for an alkylene group of the formula $-(CH_2)_p-$, and p is an integer from 1 to 6.

8. The silane according to claim 1, wherein each $R^3$ independently of one another stands for a group of the formula (3), where $R^8$ stands for a group of the formula (4), each $R^{11}$ independently of one another stands for a substituted or unsubstituted alkyl group having 1 to 10 carbon atoms, and/or each $R^{12}$ independently of one another stands for a substituted or unsubstituted alkyl group having 1 to 10 carbon atoms.

9. The silane according to claim 1, wherein each $R^3$ independently of one another stands for a group of the formula (3), $R^8$ stands for a group of the formula (4), and o stands for 0 or 1.

10. The silane according to claim 1, wherein m is 0 or 1, and/or n is 0, 1 or 2.

11. A method for preparing a silane according to claim 1, comprising:
reacting a silane of the formula (5), $$\text{Si}(R^1)_m(R^2)_{4-m} \quad (5)$$

where
m, and each $R^1$ and each $R^2$, in each case independently of one another, have the meanings given in claim 1, and at least one aminosilane compound of the general formula (6):

$$(HR^7N)\text{—}R^{10}\text{—}SiR^{11}{}_o(OR^{12})_{3-o} \quad (6)$$

where
o, $R^7$, $R^{10}$, and each $R^{11}$ and each $R^{12}$, in each case independently of one another, have the meanings given in claim 1.

12. The method according to claim 11, wherein the molar ratio of the silane of the formula (5) to the aminosilane compound of the general formula (6) is 2:1 to 30:1.

13. The method according to claim 11, comprising stirring the silane of the formula (5) and the aminosilane compound of the general formula (6) at 1 bar pressure and a temperature of 40 to 80° C., for at least 10 minutes.

14. A curable composition comprising at least one silane according to claim 1 and at least one polyorganosiloxane, whereby the polyorganosiloxane has at least one hydroxy group bound to a silicon atom.

15. The curable composition according to claim 14, further comprising at least one tin curing catalyst.

* * * * *

UNITED STATES PATENT AND TRADEMARK OFFICE
CERTIFICATE OF CORRECTION

PATENT NO. : 10,487,096 B2
APPLICATION NO. : 15/702820
DATED : November 26, 2019
INVENTOR(S) : Andrea Gutacker and Johann Klein It is certified that error appears in the above-identified patent and that said Letters Patent is hereby corrected as shown below:

In the Specification

Column 7, Line 56: Change "—$R^{10}$—$SiR^{10}_o(OR^{12})_{3-o}$" to -- -$R^{10}$-$SiR^{11}_o(OR^{12})_{3-o}$ --.

Column 8, Line 58: Change "Re" to -- R6 --.

Column 15, Line 23: Change "methyltnrimethoxysilane" to -- methyltrimethoxysilane --.

Column 15, Line 29: Change "10 Trimethoxy" to -- IO Trimethoxy --.

Column 15, Line 30: Change "10 Triethoxy" to -- IO Triethoxy --.

Column 22, Line 47: Change "N/m]" to -- N/m2] --.

Signed and Sealed this
First Day of September, 2020

Andrei Iancu
*Director of the United States Patent and Trademark Office*